(12) United States Patent
Ozaki et al.

(10) Patent No.: US 7,940,967 B2
(45) Date of Patent: May 10, 2011

(54) MEDICAL PROCEDURE SUPPORT SYSTEM AND METHOD

(75) Inventors: Takashi Ozaki, Hachioji (JP); Koichi Tashiro, Sagamihara (JP); Akinobu Uchikubo, Iruma (JP); Takeaki Nakamura, Hino (JP)

(73) Assignee: Olympus Corporation, Tokyo (JP)

( * ) Notice: Subject to any disclaimer, the term of this patent is extended or adjusted under 35 U.S.C. 154(b) by 986 days.

(21) Appl. No.: 11/092,343

(22) Filed: Mar. 29, 2005

(65) Prior Publication Data

US 2005/0215854 A1 Sep. 29, 2005

(30) Foreign Application Priority Data

Mar. 29, 2004 (JP) ................................. 2004-097125

(51) Int. Cl.
*G06K 9/00* (2006.01)
(52) U.S. Cl. ...................................................... 382/128
(58) Field of Classification Search .................. 382/141, 382/151, 152, 254, 276, 128, 294; 600/117
See application file for complete search history.

(56) References Cited

U.S. PATENT DOCUMENTS

| 5,776,050 | A | * | 7/1998 | Chen et al. | ..................... | 600/117 |
| 5,878,159 | A | * | 3/1999 | Taleblou et al. | .............. | 382/128 |
| 5,982,953 | A | * | 11/1999 | Yanagita et al. | .............. | 382/294 |

FOREIGN PATENT DOCUMENTS

| JP | 09-035043 | 2/1997 |
| JP | 2000-135215 | 5/2000 |
| JP | 2001-198136 | 7/2001 |
| JP | 2003-265408 | 9/2003 |

OTHER PUBLICATIONS

Japanese Official Action dated Nov. 17, 2009.

* cited by examiner

*Primary Examiner* — Vu Le
*Assistant Examiner* — Claire Wang
(74) *Attorney, Agent, or Firm* — Scully, Scott, Murphy & Presser, P.C.

(57) ABSTRACT

A medical procedure support system of the invention includes an endoscope for obtaining images of an internal part of the body cavity of a subject, an endoscopic image creating unit for creating an endoscopic image obtained by the endoscope, an image reading unit for reading a virtual image relating to the subject and a reference image relating to the virtual image, a superimposition commanding unit for commanding to superimpose the reference image on at least one of the virtual image and the endoscopic image, and a combined image creating unit for performing the superimposition of the reference image data commanded by the superimposition commanding unit and creating a combined image thereof.

7 Claims, 17 Drawing Sheets

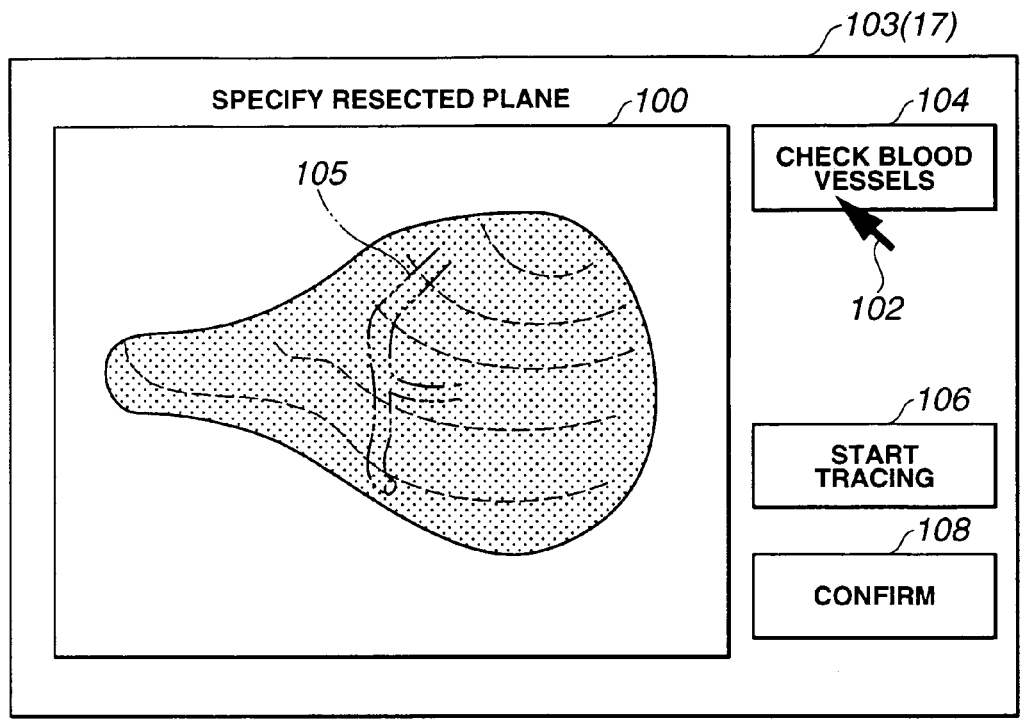
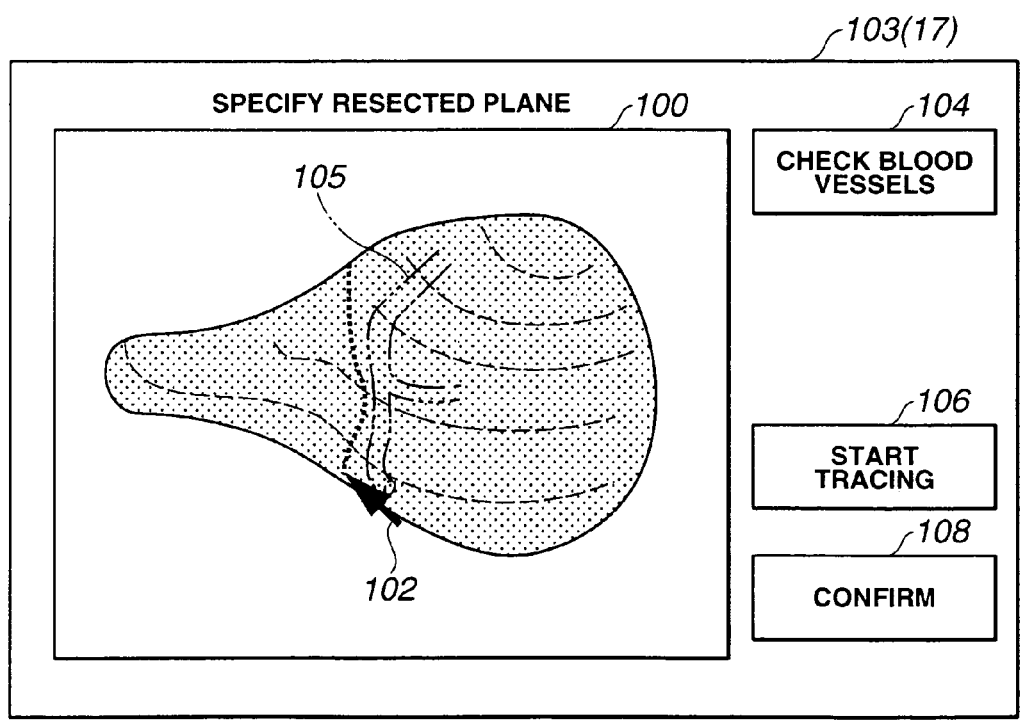

MEDICAL PROCEDURE SUPPORT SYSTEM AND METHOD

This application claims benefit of Japanese Application No. 2004-97125 filed on Mar. 29, 2004, the contents of which are incorporated by this reference.

BACKGROUND OF THE INVENTION

1. Field of the Invention

The present invention relates to a medical procedure support system and method for supporting a medical procedure by creating virtual image data relating to a subject and based on the virtual image data.

2. Description of the Related Art

In recent years, diagnoses using images have been widely performed. Three-dimensional virtual image data of an internal part of a subject is obtained by picking up tomographic images of the subject by, for example, an X-ray CT (Computed Tomography) apparatus. An affected part has been diagnosed by using the virtual image data.

In the CT apparatus, the apparatus for irradiating and detecting the X-ray is continuously rotated while the subject is continuously fed in the body axis direction. Thus, a helical continuous scan can be performed with respect to the three-dimensional area in the subject, and a three-dimensional virtual image can be created on the basis of tomographic images of continuous slices of the three-dimensional area.

A three-dimensional image of the bronchi of the lung is one of those three-dimensional images. A three-dimensional image of the bronchi is used for three-dimensionally locating an abnormal part, which may have a lung cancer, for example. In order to check an abnormal part by performing a biopsy, a sample of a tissue is taken by using a biopsy needle or biopsy forceps projecting from the distal part of a bronchi endoscope inserted to the body.

When the abnormal part is located close to the end of a branch, it is hard for the distal end of the endoscope to reach a target part quickly and precisely in a tract in the body having multiple branches. Accordingly, Japanese Unexamined Patent Application Publication No. 2000-135215 discloses an apparatus for navigating a bronchi endoscope to a target part. In the apparatus, a three-dimensional image of the tract in the subject is created on the basis of the image data of the three-dimensional area of the subject, and a path to a target point along the tract on the three-dimensional image is obtained. Further, a virtual endoscopic image (called virtual image, hereinafter) of the tract along the path is created on the basis of the image data and the virtual image is displayed.

Furthermore, conventionally, image analysis software has been in practical use which may be used for a diagnosis of an internal organ of an abdominal area serving as a subject by creating a three-dimensional virtual image of the subject mainly in the abdominal area and displaying the three-dimensional virtual image.

An image system using this kind of image analysis software is used by a doctor for performing a diagnosis for grasping a change in a lesion of a subject in an abdominal area, for example, of a patient before a surgery by viewing a virtual image thereof, which is generally performed outside of an operation room such as a conference room.

SUMMARY OF THE INVENTION

A medical procedure support system according to a first aspect of the present invention includes an endoscope for obtaining images of an internal part of the body cavity of a subject, an endoscopic image creating unit for creating an endoscopic image obtained by the endoscope, an image reading unit for reading a virtual image relating to the subject and a reference image relating to the virtual image, a superimposition commanding unit for commanding to superimpose the reference image on at least one of the virtual image and the endoscopic image, and a combined image creating unit for performing the superimposition of the reference image data commanded by the superimposition commanding unit and creating a combined image thereof.

A medical procedure support system according to a second aspect of the present invention includes an area specifying unit for specifying a selected area on a virtual image relating to a subject, an area information storing unit for storing area information of the selected area specified by the area specifying unit associated with the virtual image, and an area image creating unit for creating an area image of the selected area based on the area information.

A medical procedure support system according to a third aspect of the present invention includes an endoscope for obtaining images of an internal part of the body cavity of a subject, an endoscopic image creating unit for creating an endoscopic image obtained by the endoscope, and an image superimposing unit for superimposing an area image on the endoscopic image or virtual image.

Another aspect of the present invention, there is provided a medical procedure support method which includes an endoscopic image creating step of creating an endoscopic image obtained by an endoscope for picking up images of an internal part of the body cavity of a subject, an image reading step of reading a virtual image relating to the subject and a reference image relating to the virtual image, a virtual image creating step of creating the virtual image and the reference image, a superimposition commanding unit of commanding to superimpose the reference image on at least one of the virtual image and the endoscopic image, a combined image creating unit of performing the superimposition of the commanded reference image data and creating a combined image thereof, and a combined image display step of displaying the combined image on a monitor placed in an operation room.

BRIEF DESCRIPTION OF THE DRAWINGS

FIG. 6 is a second diagram for explaining the flowchart in FIG. 4;

FIG. 7 is a third diagram for explaining the flowchart in FIG. 4;

DESCRIPTION OF THE PREFERRED EMBODIMENTS

Preferred embodiments of the invention will be described below with reference to drawings.

First Embodiment

Figure 1:
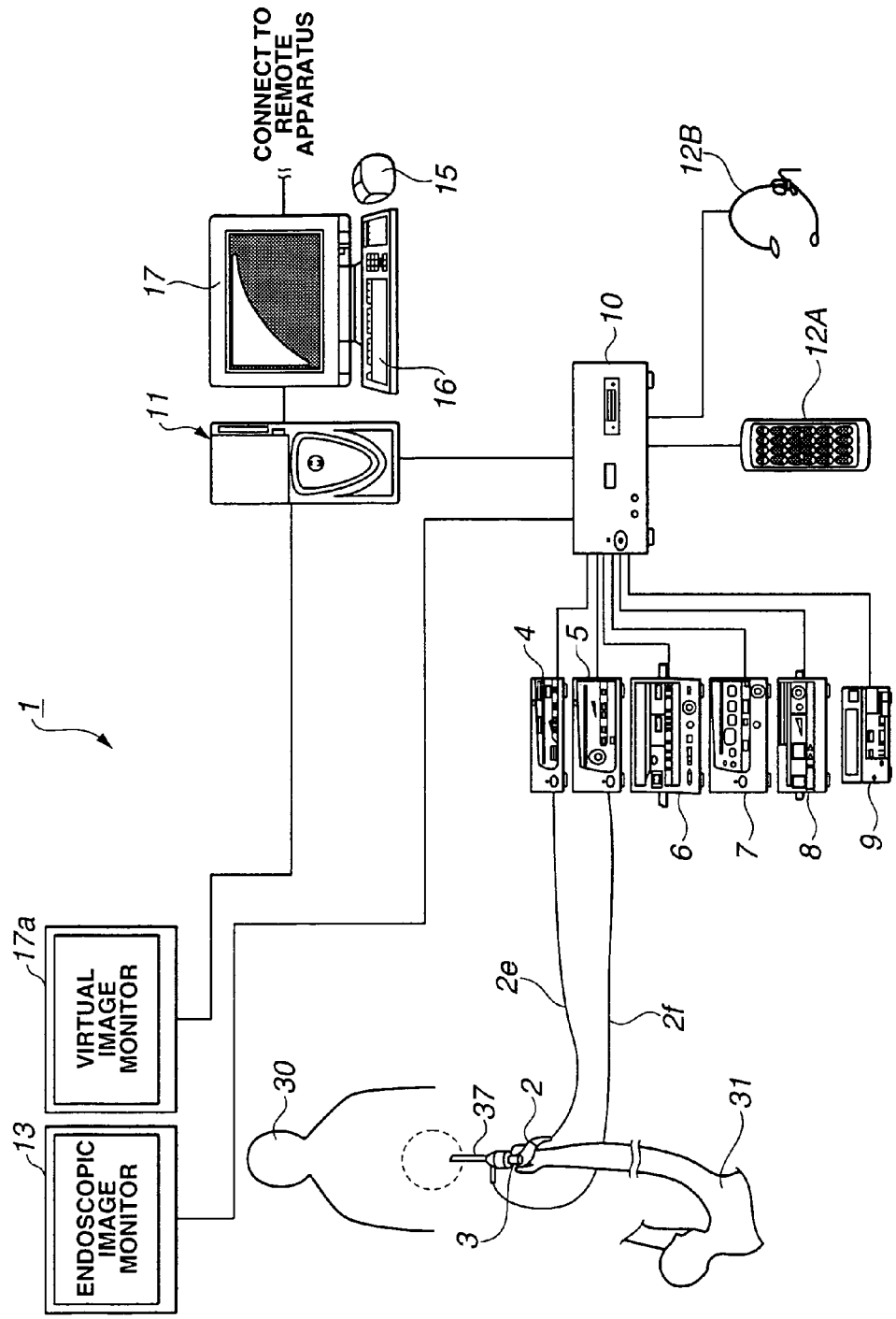
FIG. 1 is a construction diagram showing a construction of a medical procedure support system according to a first embodiment of the invention.
Figure 2:
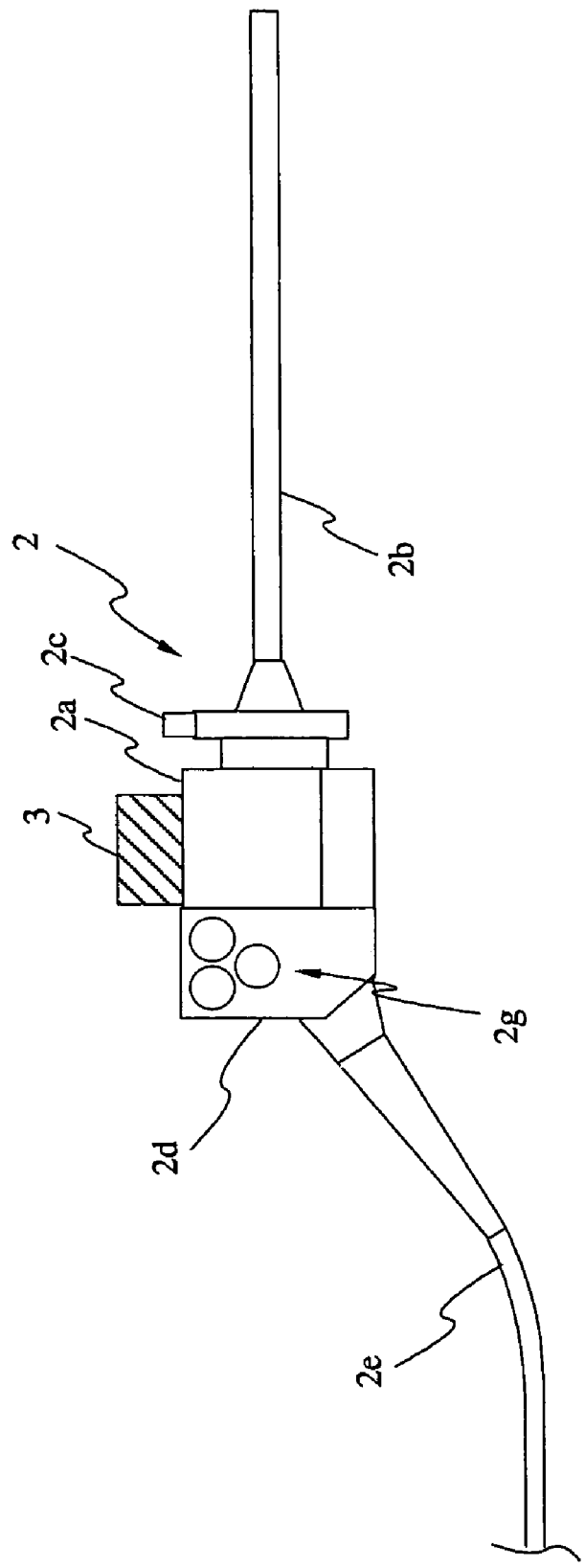
FIG. 2 is a diagram showing a construction of the endoscope in FIG. 1.
Figure 3:
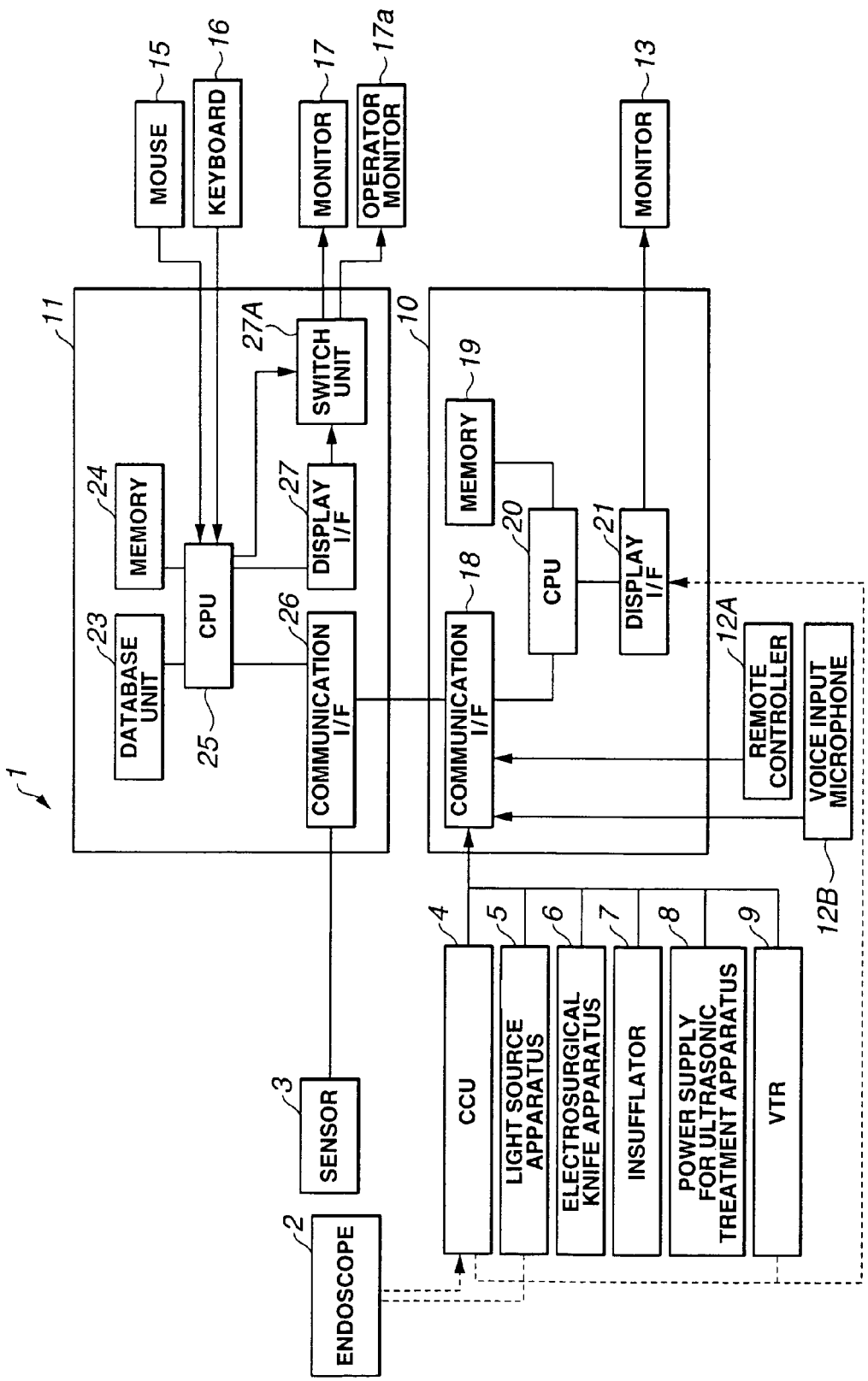
FIG. 3 is a block diagram showing a construction of the main part of the medical procedure support system in FIG. 1.
Figure 4:
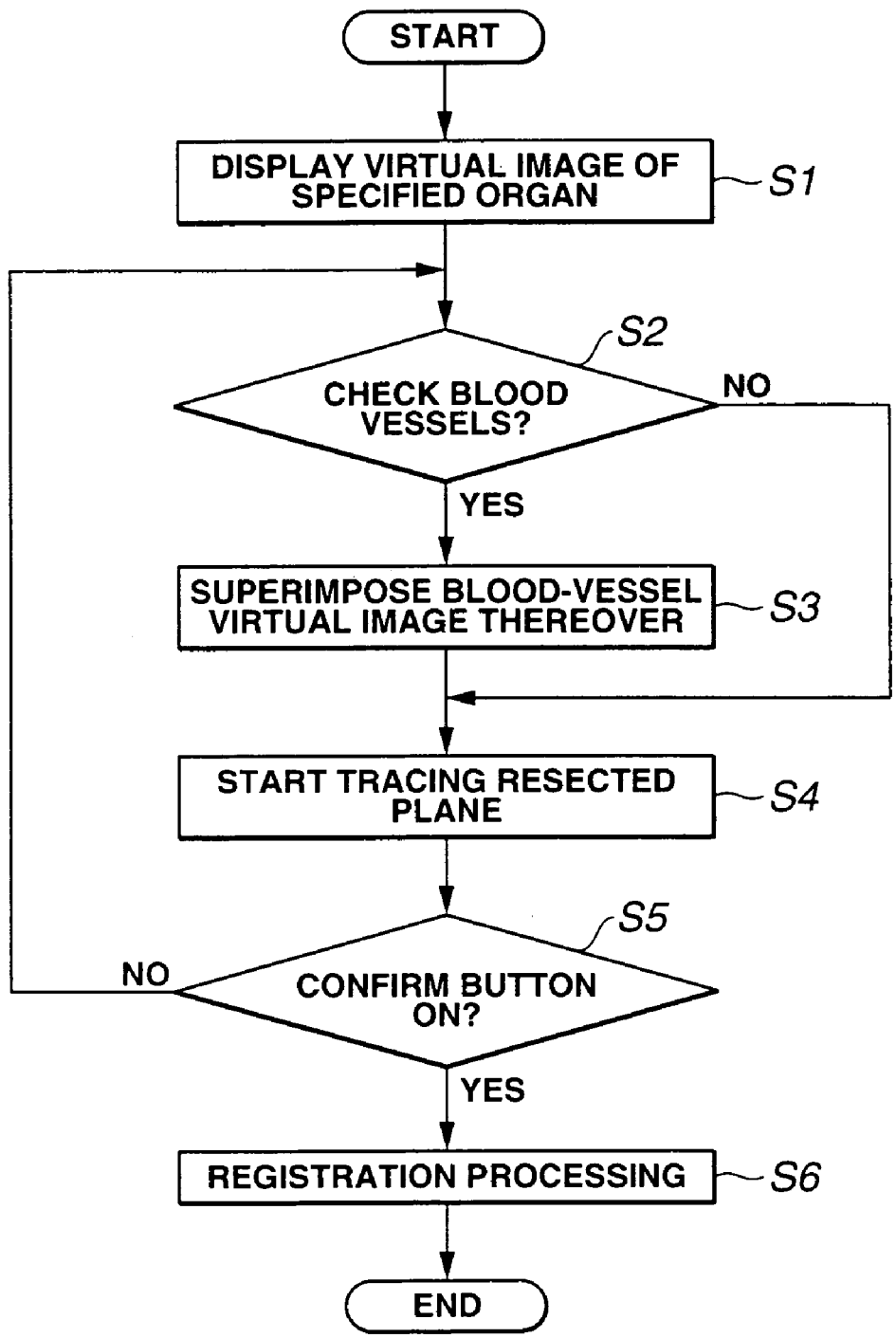
FIG. 4 is a flowchart describing an operation before a medical procedure of the virtual image creating unit in FIG. 1.
Figure 5:
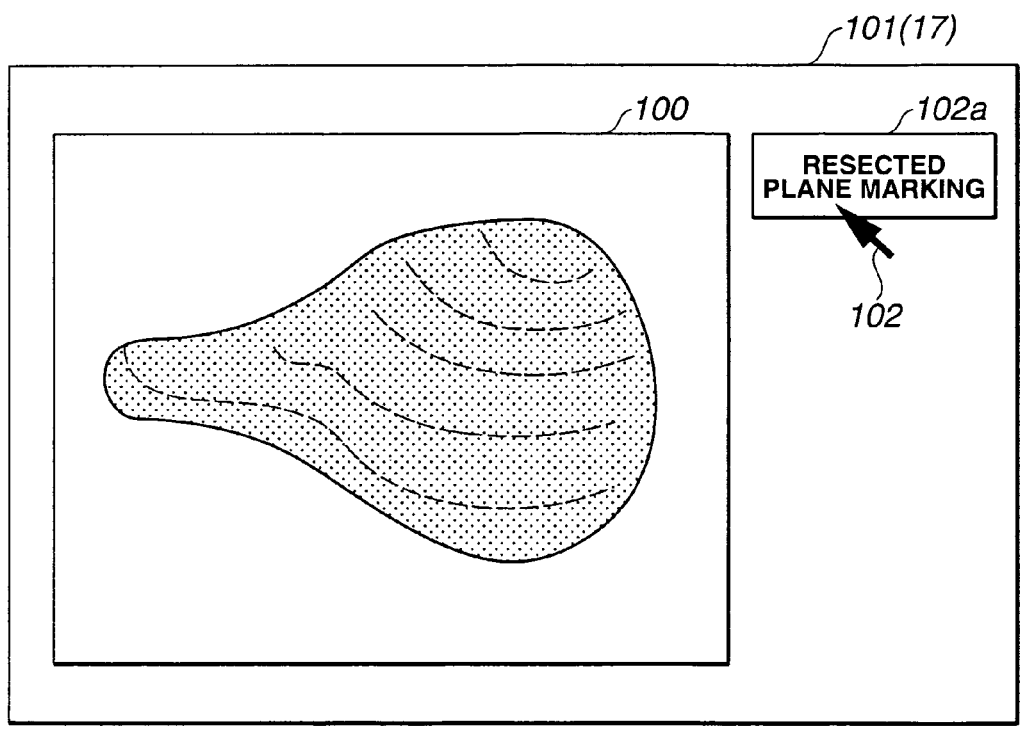
FIG. 5 is a first diagram for explaining the flowchart in FIG. 4.
Figure 8:
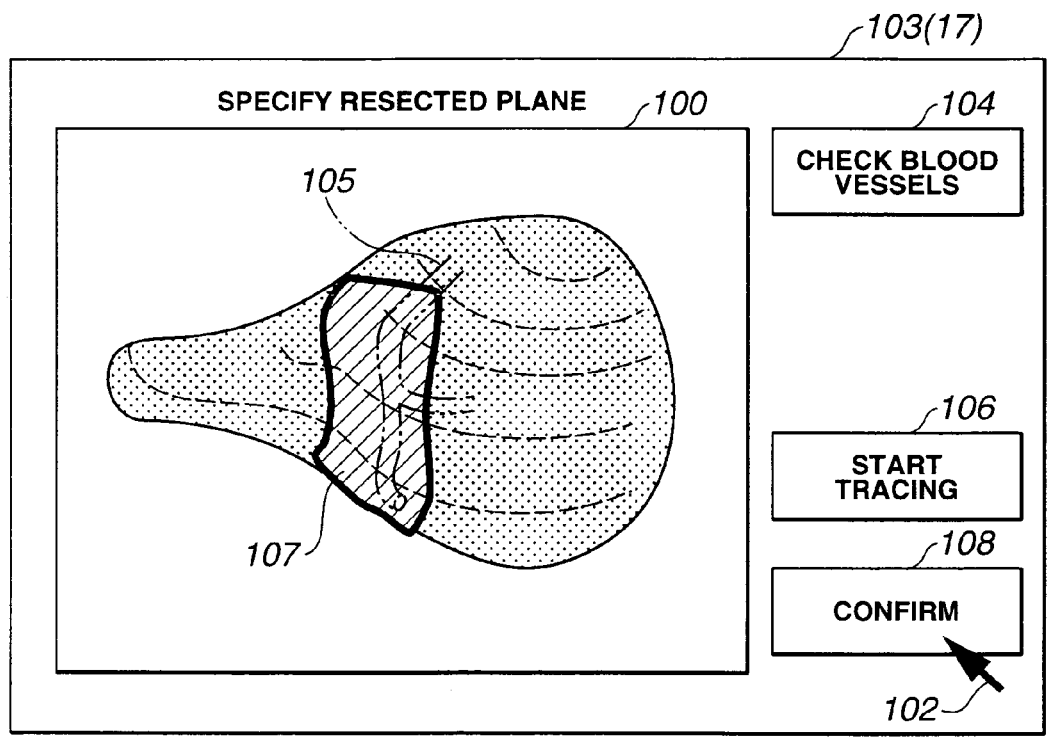
FIG. 8 is a fourth diagram for explaining the flowchart in FIG. 4.
Figure 9:
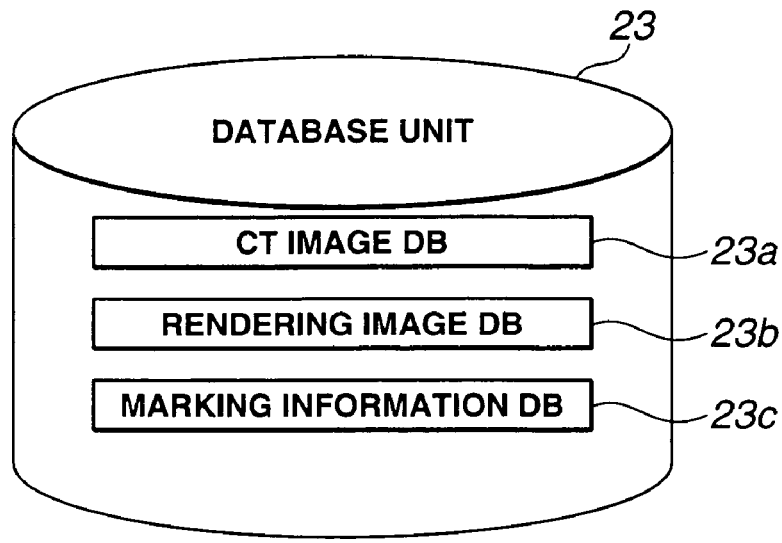
FIG. 9 is a diagram illustrating a database to be established in the database unit in FIG. 1.
Figure 10:
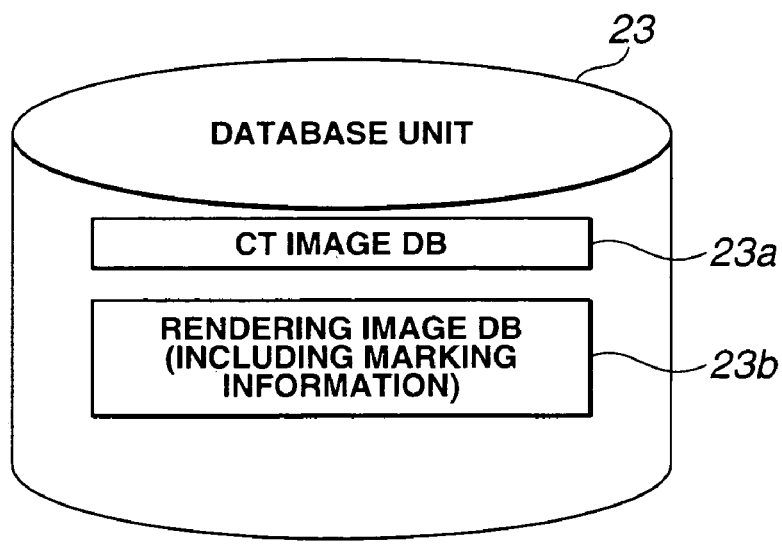
FIG. 10 is a diagram illustrating a variation example of the database to be established in the database unit in FIG. 1.
Figure 11:
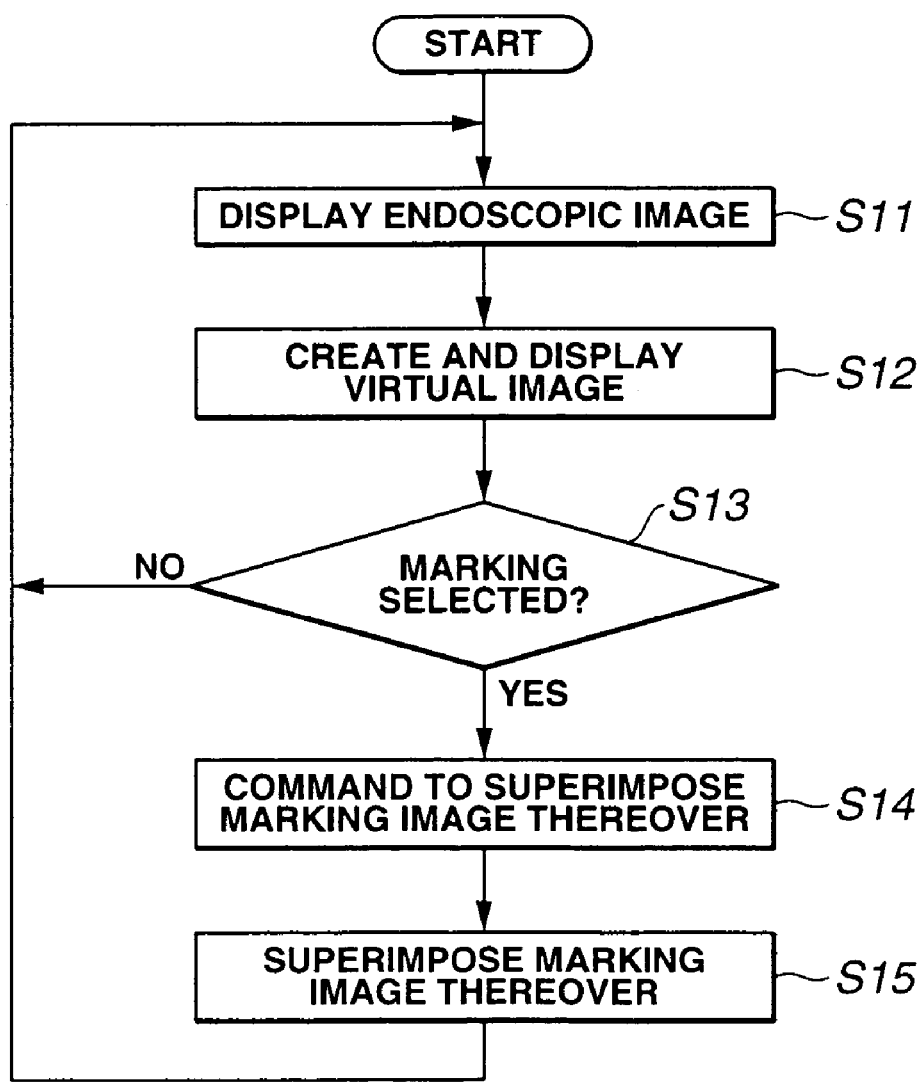
FIG. 11 is a flowchart describing an operation during a medical procedure of the medical procedure support system in FIG. 1.
Figure 12:
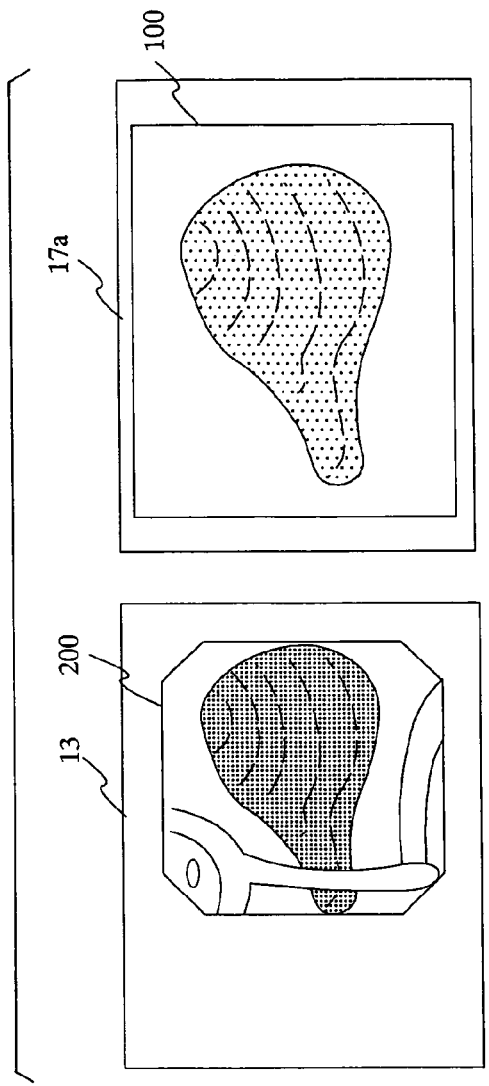
FIG. 12 is a first diagram showing images displayed on a virtual image monitor based on the flowchart in FIG. 11.
Figure 13:
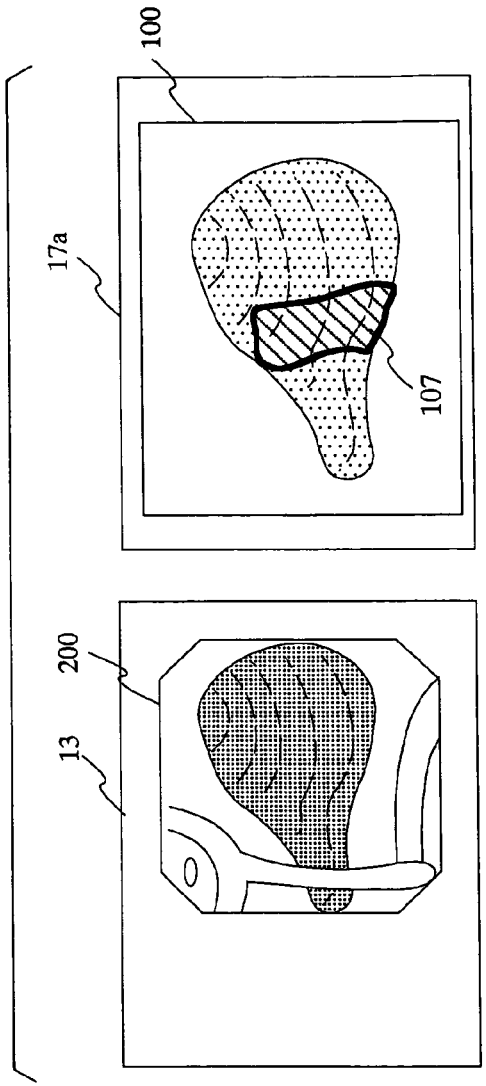
FIG. 13 is a second diagram showing images displayed on the virtual image monitor based on the flowchart in FIG. 11.
Figure 14:
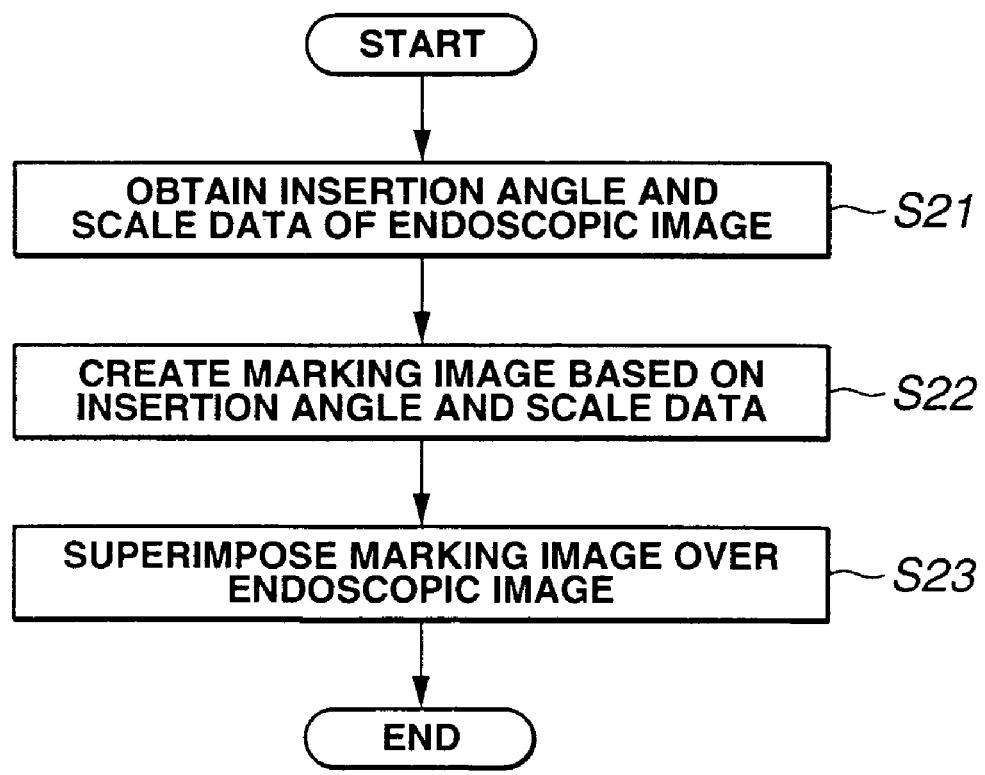
FIG. 14 is a flowchart describing a variation example of an operation during a medical procedure of the medical procedure support system in FIG. 1.
Figure 15:
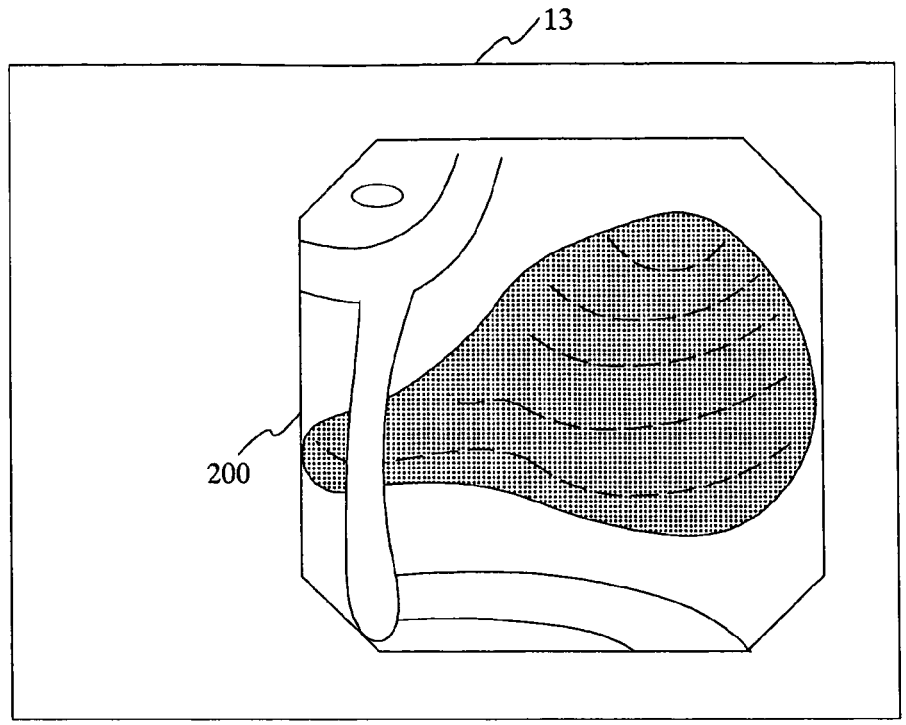
FIG. 15 is a first diagram showing an image displayed on an endoscopic image monitor based on the flowchart in FIG. 14.
Figure 16:
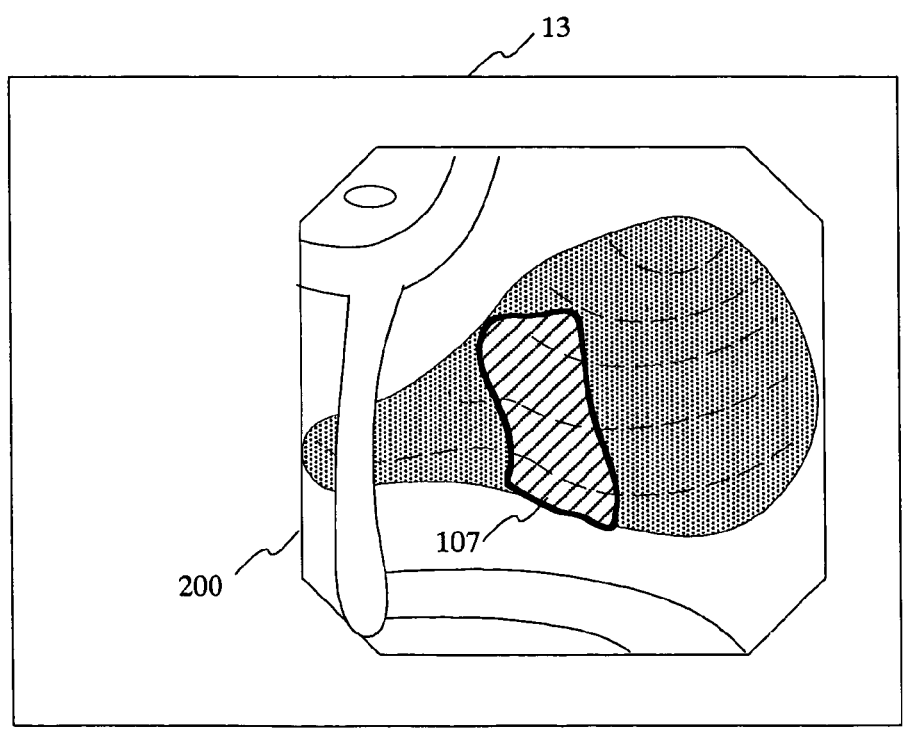
FIG. 16 is a second diagram showing an image displayed on the endoscopic image monitor based on the flowchart in FIG. 14.

FIGS. 1 to 16 relate to a first embodiment of the invention; FIG. 1 is a construction diagram showing a construction of a medical procedure support system; FIG. 2 is a diagram showing a construction of the endoscope in FIG. 1; FIG. 3 is a block diagram showing a construction of the main part of the medical procedure support system in FIG. 1; FIG. 4 is a flowchart describing an operation before a medical procedure of the virtual image creating unit in FIG. 1; FIG. 5 is a first diagram for explaining the flowchart in FIG. 4; FIG. 6 is a second diagram for explaining the flowchart in FIG. 4; FIG. 7 is a third diagram for explaining the flowchart in FIG. 4; FIG. 8 is a fourth diagram for explaining the flowchart in FIG. 4; FIG. 9 is a diagram illustrating a database to be established in the database unit in FIG. 1; FIG. 10 is a diagram illustrating a variation example of the database to be established in the database unit in FIG. 1; FIG. 11 is a flowchart describing an operation during a medical procedure of the medical procedure support system in FIG. 1; FIG. 12 is a first diagram showing images displayed on a virtual image monitor based on the flowchart in FIG. 11; FIG. 13 is a second diagram showing images displayed on the virtual image monitor based on the flowchart in FIG. 11; FIG. 14 is a flowchart describing a variation example of an operation during a medical procedure of the medical procedure support system in FIG. 1; FIG. 15 is a first diagram showing an image displayed on an endoscopic image monitor based on the flowchart in FIG. 14; and FIG. 16 is a second diagram showing an image displayed on the endoscopic image monitor based on the flowchart in FIG. 14.

As shown in FIG. 1, a medical procedure support system 1 of this embodiment is combined with an endoscope system and, more specifically, includes an endoscope 2 serving as an observing unit by which an internal part of the body cavity of a subject can be observed, a CCU 4, a light source apparatus 5, an electrosurgical knife apparatus 6, an insufflator 7, a power supply 8 for an ultrasonic treatment apparatus, a VTR 9, a system controller 10, a virtual image creating unit 11, a remote controller 12A, a voice input microphone 12B, a mouse 15, a keyboard 16, a virtual image display monitor 17, an endoscopic image monitor 13, and a virtual image monitor 17a. The endoscopic image monitor 13 and the virtual image monitor 17a are placed in an operation room.

According to this embodiment, a laparoscope as shown in FIG. 2 is used as the endoscope 2. The endoscope (that is, laparoscope) 2 includes an insertion section 2b to be inserted into the abdominal cavity of a subject and a grip section 2a provided on the proximal side of the insertion section 2b. An illumination optical system and an observation optical system are provided in the insertion section 2b. The illumination optical system illuminates an observing part in the abdominal cavity of the subject and the observation optical system obtains an observation image of an internal part of the abdominal cavity of the subject.

The grip section 2a includes a light guide connector 2c. The light guide connector 2c is connected to one end of a light guide cable 2f (see FIG. 1) having the other end connecting to the light source apparatus 5, whereby illumination light from the light source apparatus 5 through the illumination optical system in the insertion section 2b can be irradiated to an observed part.

A camera head 2d having an image pickup unit such as a CCD is connected to an eyepiece, not shown, provided in the grip section 2a, and the camera head 2d includes a remote switch 2g for performing an operation such as zooming-in/-out of an observed image. A camera cable 2e extends on the proximal side of the camera head 2d, and a connector (not shown) is provided at the other end of the camera cable 2e. The connector is used for electrically connecting to the CCU 4.

Referring back to FIG. 1, the insertion section 2b of the endoscope 2 is inserted in a trocar 37 during an operation. The insertion section 2b is inserted to an abdominal area in the body of a patient while being held by the trocar 37. The endoscope 2 picks up image of the abdominal area by the image pickup unit such as a CCD, and the obtained image signal is supplied to the CCU 4 through the camera head 2d.

The CCU 4 performs signal processing on the image signal from the endoscope 2 and supplies image data (such as endoscopic live image data) based on the image signal to the system controller 10 placed in an operation room. Under the control of the system controller 10, image data based on the live still image or moving image from the endoscope 2 is selectively output from the CCU 4 to the VTR 9. The detail construction of the system controller 10 will be described later.

The VTR 9 can record or play endoscopic live image data from the CCU 4 under the control of the system controller 10. In playing processing, played endoscopic live image data is output to the system controller 10.

The light source apparatus 5 is a light source apparatus for supplying illumination light to the endoscope 2 through a light guide.

The electrosurgical knife apparatus 6 is an operation treating apparatus for resecting an abnormal part in an abdominal area of a patient, for example, by using an electrosurgical knife probe (not shown) with high frequency current. The power supply 8 for an ultrasonic treatment apparatus supplies the power to an operation treating apparatus for resecting or coagulating the abdominal part by using an ultrasonic probe (not shown).

The insufflator 7 includes an air-supply/suction unit, not shown, and supplies carbon dioxide gas to an abdominal area, for example, in a patient body through the trocar 37 connected thereto.

The light source apparatus 5, electrosurgical knife apparatus 6, insufflator 7 and power supply 8 for an ultrasonic treatment apparatus are electrically connected to the system controller 10 and are driven under the control of the system controller 10.

The system controller 10, endoscopic image monitor 13 and virtual image monitor 17a are placed in an operation room in addition to equipment such as the CCU 4, VTR 9, light source apparatus 5, electrosurgical knife apparatus 6, insufflator 7 and power supply 8 for an ultrasonic treatment apparatus.

According to this embodiment, an operator 31 inserts the insertion section 2b to an abdominal part of a patient 30 through the trocar 37 to obtain an image of the subject and performs a treatment on the patient 30 at a position as shown in FIG. 1. In this case, the endoscopic image monitor 13 and virtual image monitor 17a are placed at the positions where the operator 31 looks at easily (in the field-of-view direction).

The system controller 10 controls operations (such as display control and dimming control) of the entire endoscope system. The system controller 10 has, as shown in FIG. 3, a communication interface (called communication I/F, hereinafter) 18, a memory 19, a CPU 20 serving as a controller, and a display interface (called display I/F, hereinafter) 21.

The communication I/F 18 is electrically connected to the CCU 4, light source apparatus 5, electrosurgical knife apparatus 6, insufflator 7, power supply 8 for an ultrasonic treatment apparatus, VTR 9 and a virtual image creating unit 11. Transmission and reception of drive control signals or transmission and reception of endoscopic image data are controlled by the CPU 20. The communication I/F 18 is electrically connected to the remote controller 12A and voice input microphone 12B for the operator. Both serve as remote control units. The communication I/F 18 receives an operation command signal from the remote controller 12A or a voice command signal from the voice input microphone 12B and supplies the received signal to the CPU 20.

The remote controller 12A has a white-balance button, an insufflation button, a pressure button, a record button, a freeze button, a release button, a display button, operation buttons, a display color button, a tracking button, and a numeric keypad, not shown. The white balance button is used for an image displayed on the endoscopic image monitor 13 for an endoscopic live image, for example, or virtual image monitor 17 or 17a. The insufflation button is used for operating the insufflator 7. The pressure button is used for adjusting to increase or decrease pressure to be used for an insufflator. The record button is used for recording an endoscopic live image in the VTR 9. The freeze button and release button are used during a recording operation. The display button is used for displaying an endoscopic live image or virtual image. The operation buttons are used for implementing two-dimensional display (2D-display) in an operation for creating a virtual image (such as axial, coronal and sagittal buttons corresponding to a 2D-display mode). The operation buttons are used for implementing three-dimensional display (3D-display) in an operation for displaying a virtual image. The display color button is used for changing a display color. The tracking button is used for performing tracking. The operation buttons are used for switching and determining setting input information for an operation setting mode determined in accordance with a button pressed. The numeric keypad is used for inputting a numeric value, for example.

The operation buttons for implementing three-dimensional display described above include: an insertion point button for indicating the direction of the field of view of three-dimensionally displayed virtual image (information on insertion of the endoscope 2 to an abdominal area, that is, for displaying values in the X, Y and Z directions of the abdominal area to which the endoscope 2 is inserted); a focus point button (a button for displaying a value of the axial direction (angle) of the endoscope 2 inserted in the abdominal area); and buttons for commanding to change a display scale on a 3D display (such as a zoom-out button for reducing the display scale and a zoom-in button for increasing the display scale).

Thus, an operator can use the remote controller 12A including these buttons (or a switch) to operate to obtain desired information quickly.

The memory 19 stores image data of endoscopic still images, for example, and data such as equipment setting information, and the data can be stored and read under the control of the CPU 20.

The display I/F 21 is electrically connected to the CCU 4, VTR 9 and endoscopic image monitor 13 and transmits and receives endoscopic live image data from the CCU 4 or endoscopic image data played by the VTR 9 and outputs the received endoscopic live image data, for example, to the endoscopic image monitor 13. Thus, the endoscopic image monitor 13 displays an endoscopic live image based on the supplied endoscopic live image data.

The endoscopic image monitor 13 can also display an equipment setting of the endoscope system and/or setting information such as a parameter in addition to the display of an endoscopic live image under the display control of the CPU 20.

The CPU 20 performs various operations in the system controller 10, that is, the transmission and reception control of various signals via the communication I/F 18 and display I/F 24, writing/reading control of image data to/from the memory 19, display control by the endoscopic image monitor 13 and various operation control based on an operation signal from the remote controller 12A (or a switch).

On the other hand, the virtual image creating unit 11 is electrically connected to the system controller 10.

As shown in FIG. 3, the virtual image creating unit 11 has a database unit 23 for storing a CT image and so on, a memory 24, a CPU 25, a communication I/F 26, a display I/F 27 and a switching unit 27A.

The database unit 23 includes a CT image data capturing unit (not shown) for capturing two-dimensional image data (called DICOM image data, hereinafter) obtained by a CT apparatus, not shown, for obtaining X-ray tomographic images of a patient through a portable storage medium such as an MO (Magneto-Optical disk) device and a DVD (Digital Versatile Disk) device and stores the captured DICOM image data (CT image data). The reading/writing of the DICOM image data is controlled by the CPU 25. The database unit 23 also stores a virtual image, which is a rendering image of each biological part created from the CT image data, in addition to CT image data.

The memory 24 stores data such as the DICOM image data and virtual image data created by the CPU 25 based on three-dimensional image data, and the storage and read of the data are controlled by the CPU 25.

The communication I/F 26 is connected to the communication I/F 18 of the system controller 10 and transmits and receives a control signal required for an operation to be performed by the virtual image creating unit 11 and the system controller 10 in an interlocking manner under the control of the CPU 25 so that the control signal can be captured by the CPU 25.

The display I/F 27 outputs a virtual image created under the control of the CPU 25 to the virtual image monitor 17 or 17a through the switching unit 27A. Thus, the virtual image monitor 17 or 17a displays the supplied virtual image. In this case, the switching unit 27A switches the output of a virtual image under the switching control of the CPU 25 so that the virtual image can be output to a specified one of the virtual image monitors 17 and 17a. If switching the display of a virtual image is not required, the switching unit 27A may be omitted, and a same virtual image can be displayed on both of the virtual image monitors 17 and 17a.

The CPU 25 is electrically connected to the mouse 15 and keyboard 16. The mouse 15 and keyboard 16 are operation units for inputting and/or defining setting information required for executing an operation for displaying a virtual image by the virtual image display apparatus.

The CPU 25 performs various operations in the virtual image creating unit 11, that is, the transmission and reception control of various signals via the communication I/F 26 and display I/F 27, writing/reading control of image data to/from the memory 24, display control by the monitors 17 and 17a, switching control by the switching unit 27A and various operation control based on an operation signal from the mouse 15 and/or keyboard 16.

This embodiment may be established as a remote operation support system by connecting the virtual image creating unit 11 to a remote virtual image creating unit through a communication unit.

According to this embodiment, in order to create and display a virtual image as viewed from the direction of field-of-view of the endoscope 2, the grip section 2a of the endoscope 2 includes a sensor 3 as shown in FIG. 2. The sensor 3 contains a gyrosensor, for example, and detects information of insertion angle (inserting direction) to an abdominal area of the endoscope 2, for example. The information detected by the sensor 3 is supplied to the virtual image creating unit 11 via the communication I/F 26 as shown in FIG. 3.

Though, according to this embodiment, the sensor 3 is electrically connected to the virtual image creating unit 11 by a wire (signal cable), the sensor 3 may be connected to the virtual image creating unit 11 by wireless so as to communicate data.

Next, an operation of this embodiment having the above-described construction will be described. According to this embodiment, in order to resect an organ, for example, based on a virtual image of a subject before a medical procedure, the virtual image creating unit 11 performs the processing as shown in FIG. 4 so that marking information of a resected plane to be superimposed on the virtual image can be created and the marking information can be registered with the database unit 23. The resected plane is a resected plane of a focus part of a subject, that is, a lesion part.

More specifically, in step S1, when an organ is specified through the keyboard 16, a marking screen 101 having a virtual image 100 of the specified organ is displayed on the monitor 17 as shown in FIG. 5. The virtual image creating unit 11 waits for the selection of a RESECTED PLANE MARKING button 102a by a pointer 102 through the mouse 15.

Then, when the RESECTED PLANE MARKING button 102a is selected, a SPECIFY RESECTED PLANE screen 103 as shown in FIG. 6 is displayed on the monitor 17. In step S2, whether the arrangement of blood vessels on the virtual image 100 of the SPECIFY RESECTED PLANE screen 103 is to be checked or not and whether a CHECK BLOOD VESSELS button 104 on the monitor 17 has been selected by the pointer 102 or not are determined. If the CHECK BLOOD VESSELS button 104 is selected, a blood vessel rendering image 105 is superimposed on the virtual image 100 of the SPECIFY RESECTED PLANE screen 103 (see FIG. 6) in step S3, and the processing moves to step S4. If the CHECK BLOOD VESSELS button 104 is not selected, the processing moves to step S4 directly.

Next, when a START TRACING button 106 on the SPECIFY RESECTED PLANE screen 103 is selected by the pointer 102 in step S4, a resected plane can be specified by the pointer 102 on the virtual image 100 of the SPECIFY RESECTED PLANE screen 103. Thus, manual tracing of the resected plane by using the mouse 15 as shown in FIG. 7 is started, and a resected plane marking image 107 as shown in FIG. 8, which is an image indicating a selected area, is defined on the virtual image 100. In other words, step S4 functions as an area specifying unit for specifying a selected area on a virtual image. The area to be selected is a resected plane area of a focus part of a subject, that is, a lesion part area.

Then, in step S5, whether a CONFIRM button 108 on the SPECIFY RESECTED PLANE screen 103 is selected by the pointer 102 or not is determined. If the CONFIRM button 108 is not selected, the processing returns to step S2. If the CONFIRM button 108 is selected, the resected plane is confirmed in step S6, and the resected plane marking image 107 indicating the resected plane is registered with the database unit 23. Then, the processing ends. In other words, the resected plane marking image 107 serving as a reference image associated with the virtual image 100 of the specified organ is stored in the database unit 23 serving as a storage unit. More specifically, the resected plane marking image 107 is area information of the selected area specified in step S4 functioning as the area specifying unit. The area information associated with the virtual image 100 of the specified organ is stored in the database unit 23 serving as a storage unit. Therefore, step S6 functions as an information storage control unit for storing area information.

Thus, in the database unit 23, as shown in FIG. 9, a CT image database 23a having three-dimensional image data (CT image data), a rendering image database 23b having the virtual image 100 and a marking information database 23c having the resected plane marking image 107 and marking information such as marking relative position information with respect to the virtual image 100 are established.

As shown in FIG. 10, the CT image database 23a and the rendering image database 23b may be established in the database unit 23 by including marking information in the rendering image database 23b.

In this way, after the rendering image database 23b and marking information database 23c are established, a medical procedure by an operator is started. When an observation image of an internal part of a subject is obtained by the camera head 2d, an endoscopic image 200 as shown in FIG. 12 is displayed on the endoscopic image monitor 13 in step S11 as shown in FIG. 11. Step S11 functions as an endoscopic image creating unit and endoscopic image creating step of creating an endoscopic image obtained by the endoscope 2.

Then, in step S12, the virtual image 100 is created based on information of an insertion angle to an abdominal area of the endoscope 2 from the sensor 3, and the virtual image 100 as shown in FIG. 12 is displayed on the operator virtual image monitor 17a. Thus, the virtual image 100 can serve as a supporting image corresponding to an endoscopic image in real time. Step S12 functions as a virtual image creating unit and virtual image creating step of creating a virtual image. Furthermore, step S12 is an image reading unit and image reading step of reading a virtual image from the database unit 23.

If an operator produces a voice such as "Display marking" in accordance with the development of a medical procedure in step S13, the voice input microphone 12B, for example, detects the voice in step S14, and the CPU 20 recognizes the operator's command by voice recognition processing. Then, the CPU 25 in the virtual image creating unit 11 is commanded to superimpose the resected plane marking image 107 on the virtual image 100. Step S14 functions as a resected plane marking image superimposition commanding unit and resected plane marking image superimposition commanding step of commanding to superimpose the resected plane marking image 107 on the virtual image 100.

In step S15, the CPU 25 reads marking information from the marking information database 23c, adjusts the position with respect to the virtual image 100 and superimposes the resected plane marking image 107 on the virtual image 100, as shown in FIG. 13. Step S15 functions as a combined image creating unit and combined image creating step of creating a combined image by superimposing the resected-plane marking image 107 on the virtual image 100. In other words, step S15 includes an area image creating unit for creating the resected plane marking image 107, which is an area image based on area information and functions as an image superimposing unit for superimposing the created area image on a virtual image. Step S15 further functions as a combined image display step of displaying a virtual image having the resected plane marking image 107 thereover.

According to this embodiment, during an operation, the live endoscopic image 200 is displayed on the endoscopic image monitor 13, and a virtual image varying in real time in accordance with the endoscopic image is displayed on the virtual image monitor 17a. Additionally, during an operation for resecting an organ, for example, the resected plane marking image 107 is superimposed on the virtual image 100 based on an operator's command in accordance with the development of a medical procedure. Thus, an operator can easily recognize the resected plane with reference to the virtual image reviewed before the operation and can perform a treatment of resecting the organ with reference to the resected-plane marking image 107. Therefore, a virtual image suitable for medical procedure support can be provided in real time during a medical procedure.

Though, according to this embodiment, the resected plane marking image 107 is superimposed on the virtual image 100, the present invention is not limited thereto. For example, the trocar 37 may have an encoder (not shown) such as a potentiometer for detecting an insertion amount (length) into the body of the insertion section of the endoscope 2 so that the resected plane marking image 107 can be superimposed on the endoscopic image 200 based on a scale of the endoscope image based on an amount of insertion of the insertion section of the endoscope 2 and information on an insertion angle to an abdominal area of the insertion section of the endoscope 2.

More specifically, as shown in FIG. 14, in step S21, the CPU 25 may obtain the insertion angle and scale of the live endoscopic image 200 displayed on the endoscopic image monitor 13 as shown in FIG. 15, create the resected plane marking image 107 based on the insertion angle and scale obtained in step S22, and superimpose the resected plane marking image 107 on the endoscopic image 200 as shown in FIG. 16 based on an operator's command in accordance with the development of a medical procedure in step S23. In other words, the resected plane marking image 107 may be superimposed on at least one of the virtual image 100 and the endoscopic image 200.

Second Embodiment

Figure 17:
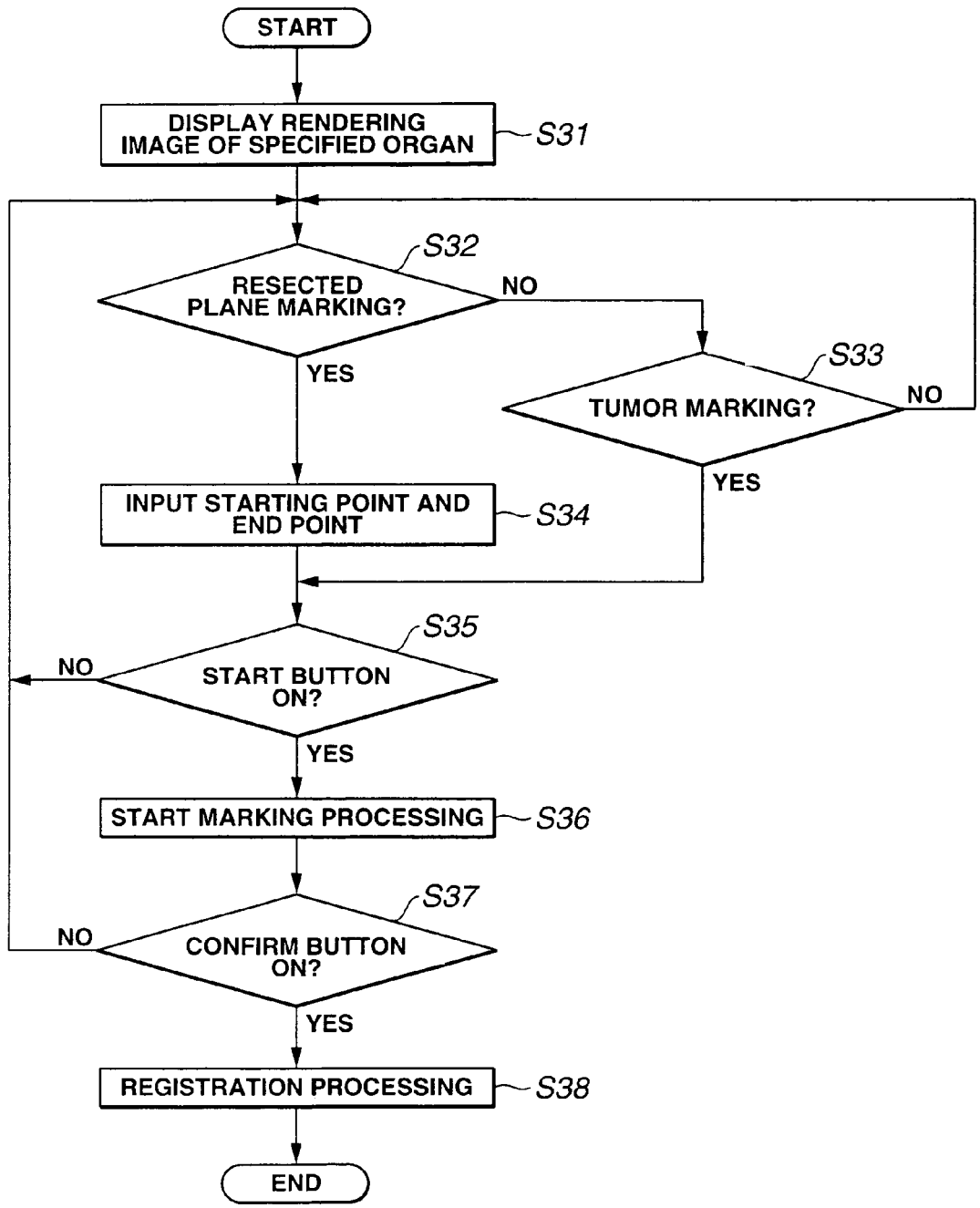
FIG. 17 is a flowchart describing an operation before a medical procedure of a virtual image creating unit according to a second embodiment of the invention.
Figure 18:
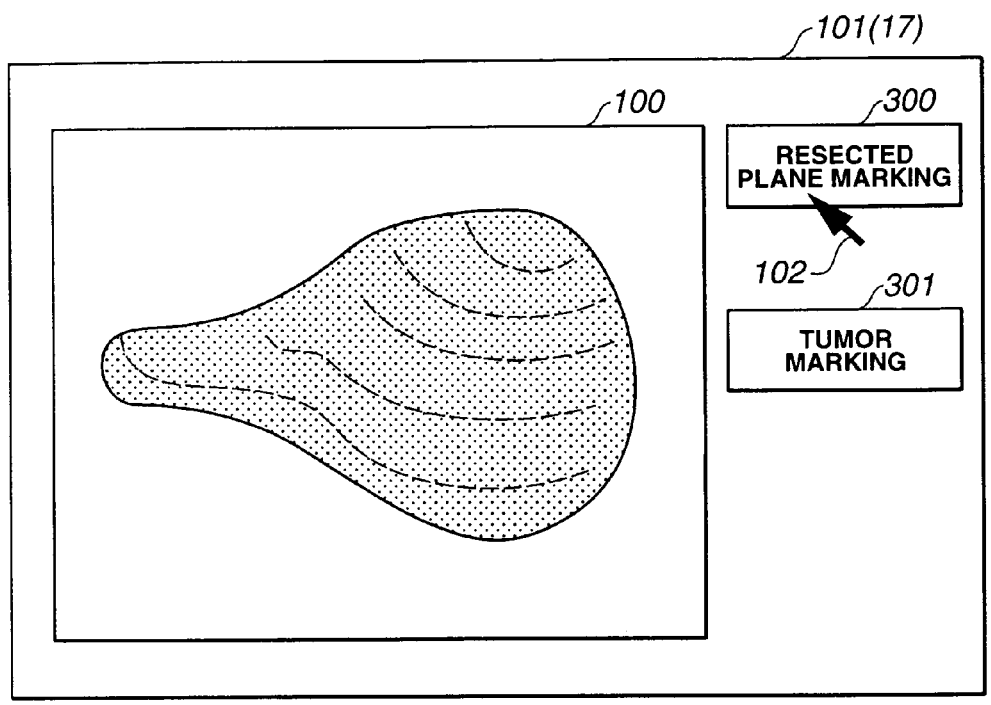
FIG. 18 is a first diagram for explaining the flowchart in FIG. 17.
Figure 19:
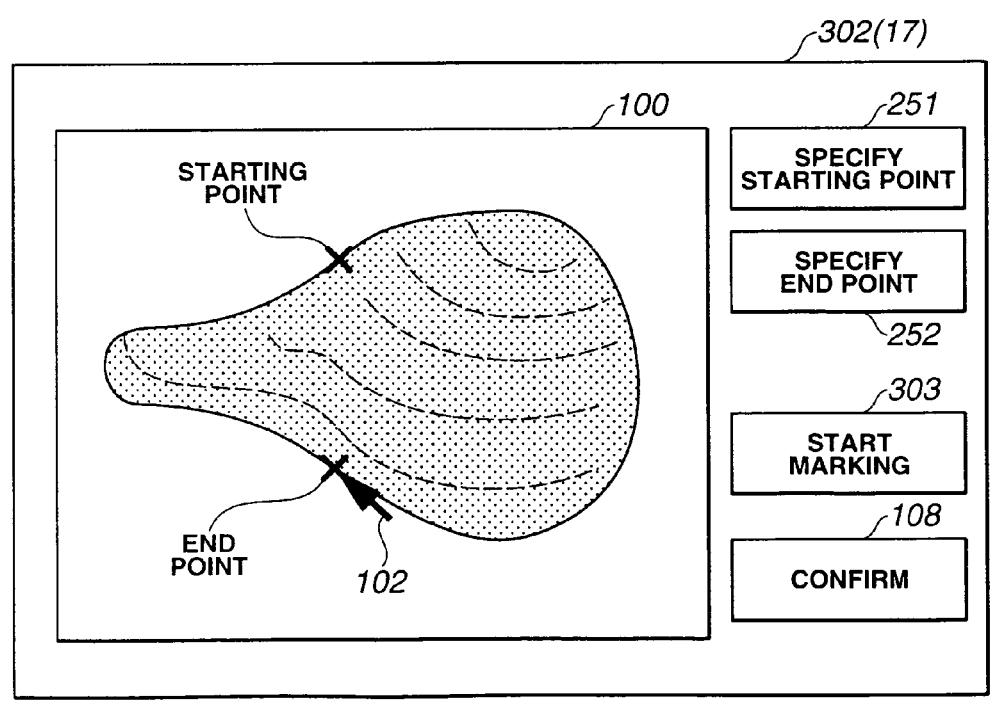
FIG. 19 is a second diagram for explaining the flowchart in FIG. 17.
Figure 20:
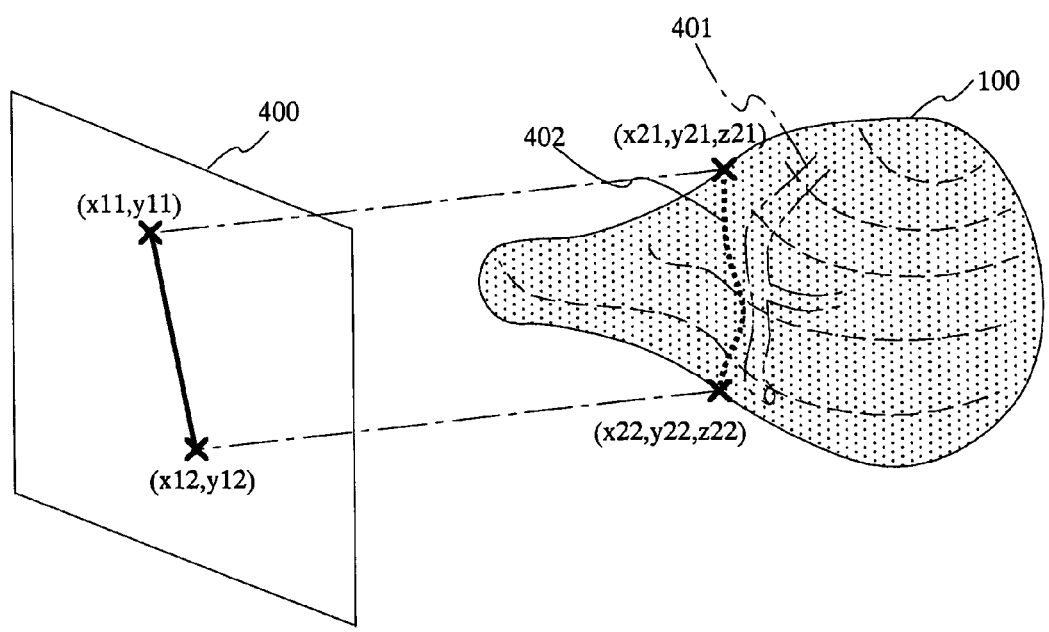
FIG. 20 is a third diagram for explaining the flowchart in FIG. 17.
Figure 21:
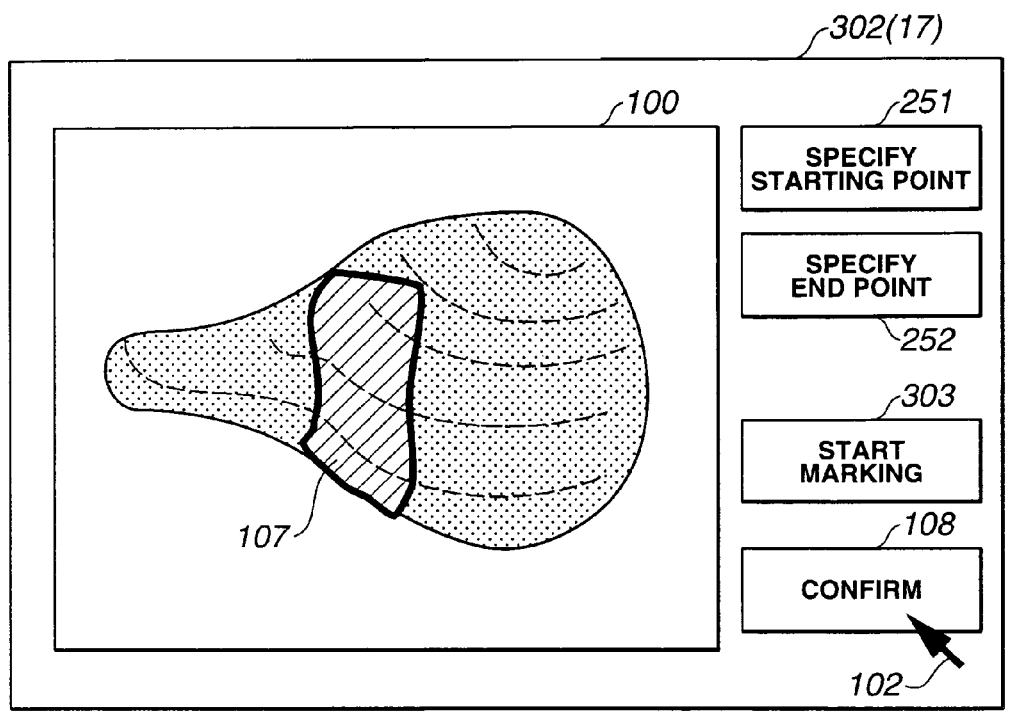
FIG. 21 is a fourth diagram for explaining the flowchart in FIG. 17.
Figure 22:
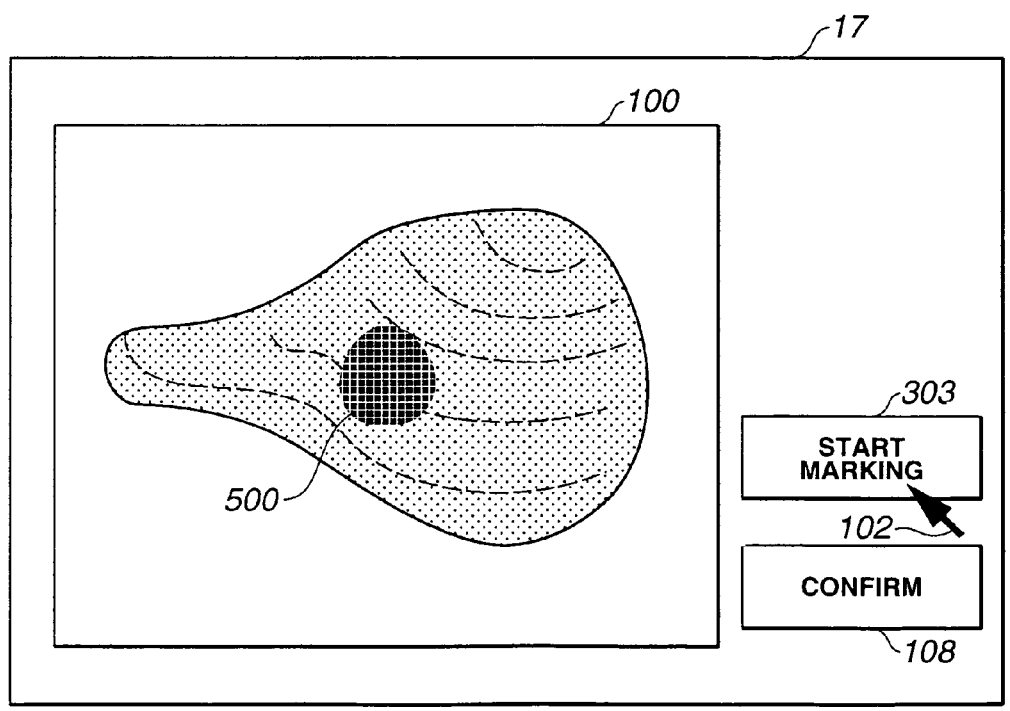
FIG. 22 is a fifth diagram for explaining the flowchart in FIG. 17.

FIGS. 17 to 22 relate to a second embodiment of the invention; FIG. 17 is a flowchart describing an operation before a medical procedure of a virtual image creating unit; FIG. 18 is a first diagram for explaining the flowchart in FIG. 17; FIG. 19 is a second diagram for explaining the flowchart in FIG. 17; FIG. 20 is a third diagram for explaining the flowchart in FIG. 17; FIG. 21 is a fourth diagram for explaining the flowchart in FIG. 17; and FIG. 22 is a fifth diagram for explaining the flowchart in FIG. 17.

Since the second embodiment is substantially identical to the first embodiment, only differences therebetween will be described.

According to this embodiment, before a medical procedure, the CPU 25 automatically extracts an organ resected plane or tumor area, for example, from a virtual image of a subject and registers a marking image indicating the resected plane and tumor area and marking information such as marking relative position information to the virtual image 100 with the marking information database 23c.

More specifically, as shown in FIG. 17, in response to the specification of an organ through the keyboard 16, for example, in step S31, the CPU 25 displays a marking screen 101 having a virtual image 100 of the specified organ on the monitor 17 as shown in FIG. 18.

Then, in steps S32 and/or S33, whether a RESECTED PLANE MARKING button 300 or TUMOR MARKING button 301 on the marking screen 101 is selected by the pointer 102 or not is determined.

If the RESECTED PLANE MARKING button 300 is selected, a resected plane marking starting screen 302 as shown in FIG. 19 is displayed on the monitor 17. Then, after two points of a starting point, which is one end of the resected plane, and an ending point, which is the other end, are specified through a SPECIFY STARTING POINT button 251 and SPECIFY END POINT button 252 on the resected plane marking starting screen 302 in step S34, the processing moves to step S35.

In step S35, the processing waits for an input through a START MARKING button 303 on the resected plane marking starting screen 302, and if the START MARKING button 303 is selected, the resected plane is automatically extracted and processing for creating a resected plane marking image is started in step S36.

The process for automatically extracting the resected plane in step S36 includes extracting a starting point (x21, y21, z21) and end point (x22, y22, z22) in a virtual three-dimensional space of the virtual image 100 with respect to a starting point (x11, y11) and end point (x12 and y12) specified on a predetermined projected plane 400 of the virtual image 100 as shown in FIG. 20, for example, calculating a curved plane including a curve 402 avoiding a blood vessel 401 in an organ, creating a resected plane marking image 107 having the calculated curved plane as the resected plane, and superimposing the resected plane marking image 107 on the virtual image 100 as shown in FIG. 21.

Then, whether the CONFIRM button 108 on the resected plane marking starting screen 302 is selected by the pointer 102 or not is determined in step S37. If the CONFIRM button 108 is not selected, the processing returns to step S32. If the CONFIRM button 108 is selected, the resected plane marking image 107 is registered with the database unit 23. Then, the processing ends.

On the other hand, if the TUMOR MARKING button 301 is selected, a tumor area is automatically extracted in step S35. The process for automatically extracting a tumor area includes extracting the outline of a tumor by performing image processing on pixel density of CT image data, and superimposing the extracted outline on the virtual image 100 on the monitor 17, which is a tumor marking image 500 serving as the tumor area, as shown in FIG. 22. The other processes are identical to the automatic creation and registration of the resected plane marking image 107.

In this way, this embodiment has an advantage that a marking image can be automatically created in addition to the advantages of the first embodiment. Furthermore, since not only a resected plane but also a tumor area can be marked, the tumor marking image 500 can be used as a real time navigation to a tumor in a treatment requiring approaching the tumor.

Figure 23:
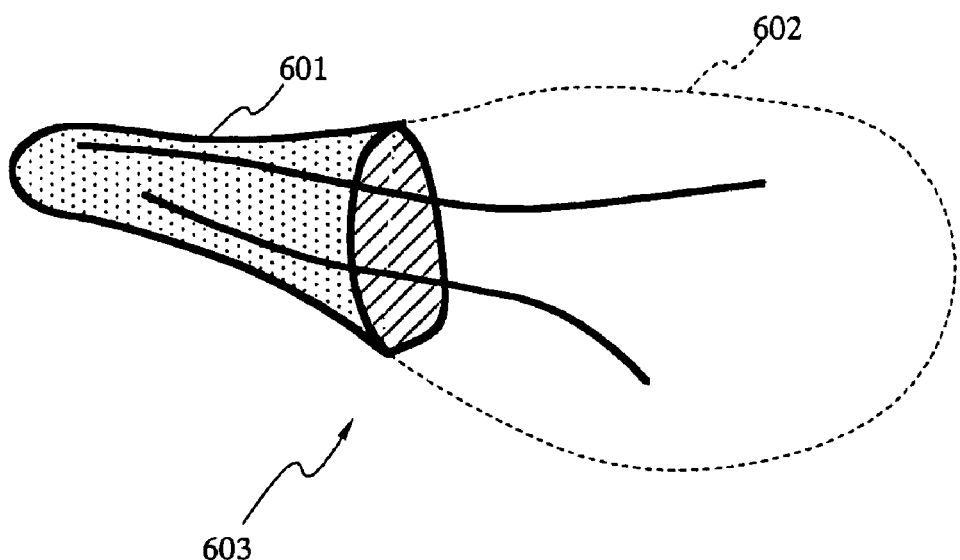
FIG. 23 is a diagram showing an example of a virtual image of an organ to be transplanted by a transplanting medical procedure to which the invention is applicable.

Though, according to this embodiment, a medical procedure is supported by a marking image superimposed on a virtual image in accordance with the development of the medical procedure, the invention is not limited thereto. For example, in transplanting an organ, for example, the virtual image creating unit 11 provided in a transplanted organ extracting facility may create a virtual image 603 including a remaining part 601 and transplanted part 602 of a transplanted organ as shown in FIG. 23 and transmit the created virtual image 603 to a transplanting medical procedure implementing facility by using communications so that the virtual image 603 can be referred in the transplanting medical procedure implementing facility.

Figure 24:
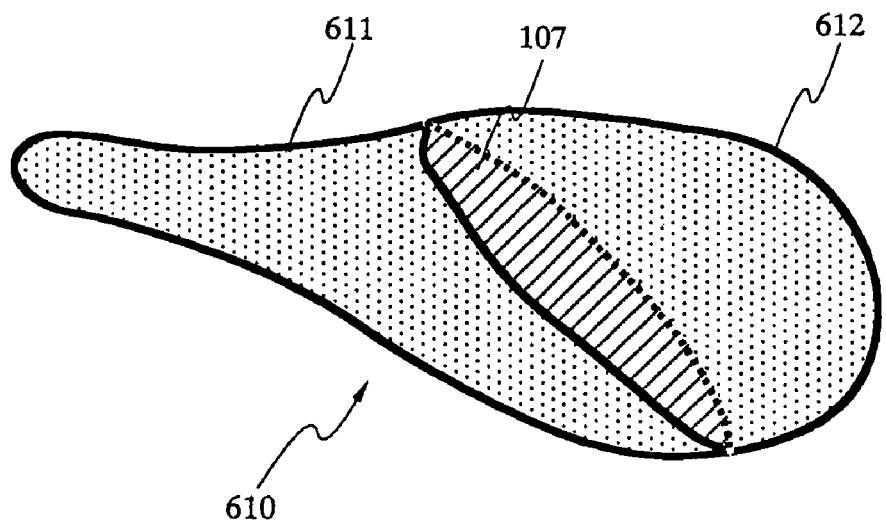
FIG. 24 is a diagram showing an example of a virtual image of an organ transplanted by a transplanting medical procedure to which the invention is applicable.

Thus, as shown in FIG. 24, the virtual image creating unit 11 in the transplanting medical procedure implementing facility can specify and register, with reference to the resected plane marking image 107, the border of the remaining part 611 and transplanted part 612 in the virtual image 610 of the transplanted organ based on the virtual image 603. Therefore, use of the resected plane marking image 107 can support a transplanting medical procedure effectively.

As described above, according to the invention, an operation support system and method can be implemented which provide a virtual image suitable for medical procedure support in real time during a medical procedure.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. A medical procedure support system, comprising:
an endoscope for obtaining live images of an internal part of the body cavity of a subject;
an endoscopic image creating unit for creating a live endoscopic image obtained by the endoscope;
an image reading unit for reading a reference virtual image relating to the internal part of the subject and a marking information of a resected plane of an organ relating to the reference virtual image, the reference virtual image and marking information being prestored in a storage unit;
a superimposition commanding unit for commanding to superimpose a marking image based on the marking information relating to the reference virtual image and an obtained insertion angle and scale of the live endoscopic image on at least one of the live endoscopic image and a live virtual image corresponding to the live endoscopic image; and
a combined image creating unit for performing the superimposition of the marking image commanded by the superimposition commanding unit and creating a combined image thereof.

2. The system according to claim 1, further comprising:
an area specifying unit for specifying a selected area on the virtual image; and
an information storage control unit for storing in the storage unit, as the marking image, an image of the selected area specified by the area specifying unit associated with the virtual image.

3. The system according to claim 2, wherein the area specifying unit specifies a resection area of a focus part of the subject in the reference virtual image as the selected area.

4. The system according to claim 2, wherein the area specifying unit specifies a lesion part area of the subject in the reference virtual image as the selected area.

5. A medical procedure support method, comprising:
an endoscopic image creating step of creating a live endoscopic image obtained by an endoscope for picking up images of an internal part of the body cavity of a subject;
an image reading step of reading a reference virtual image relating to the internal part of the subject and a marking information relating to the reference virtual image, the reference virtual image and marking information being prestored in a storage unit;
a virtual image creating step of creating the reference virtual image and further creating a marking image based on the marking information relating to the reference virtual image and an obtained insertion angle and scale of the live endoscopic image;
a superimposition commanding step of commanding to superimpose the marking image on at least one of the live endoscopic image and a live virtual image corresponding to the live endoscopic image;
a combined image creating step of performing the superimposition of the commanded marking image and creating a combined image thereof; and
a combined image display step of displaying the combined image on a monitor placed in an operation room.

6. The method according to claim 5, wherein the virtual image and the endoscopic image are displayed on different monitors placed in the operation room, and the combined image is displayed on one of the different monitors.

7. The medical procedure support system according to claim 1, further comprising a virtual image creating unit for creating the marking image based on the marking information relating to the reference virtual image and the obtained insertion angle and scale of the live endoscopic image.

* * * * *